(12) United States Patent
Hansen

(10) Patent No.: US 9,405,364 B2
(45) Date of Patent: Aug. 2, 2016

(54) METHOD OF DETERMINING REFLECTIONS OF LIGHT

(75) Inventor: Dan Witzner Hansen, Ølstykke (DK)

(73) Assignee: IT-Universitetet i København, Copenhagen S (DK)

( * ) Notice: Subject to any disclaimer, the term of this patent is extended or adjusted under 35 U.S.C. 154(b) by 341 days.

(21) Appl. No.: 13/882,476

(22) PCT Filed: Oct. 29, 2010

(86) PCT No.: PCT/EP2010/066495
§ 371 (c)(1),
(2), (4) Date: Sep. 16, 2013

(87) PCT Pub. No.: WO2012/055444
PCT Pub. Date: May 3, 2012

(65) Prior Publication Data
US 2014/0002349 A1    Jan. 2, 2014

(51) Int. Cl.
*G09G 5/00* (2006.01)
*G06F 3/01* (2006.01)
*A61B 3/113* (2006.01)
(Continued)

(52) U.S. Cl.
CPC ............... *G06F 3/013* (2013.01); *A61B 3/113* (2013.01); *G06K 9/00604* (2013.01); *G06T 7/0042* (2013.01); *G06T 7/2033* (2013.01); *G06T 2207/30201* (2013.01)

(58) Field of Classification Search
CPC .... A61B 3/113; G06F 3/013; G06K 9/00604; G06T 7/0042; G06T 7/2033; G06T 2207/30201
See application file for complete search history.

(56) References Cited

U.S. PATENT DOCUMENTS 6,120,461 A    9/2000   Smyth et al.
6,152,563 A   11/2000   Hutchinson et al.
(Continued)

FOREIGN PATENT DOCUMENTS

EP        2236074 A1    10/2010
WO    WO-2008/141460 A1   11/2008
WO    WO-2010/003410 A1    1/2010

OTHER PUBLICATIONS

International Search Report mailed Aug. 26, 2011, for PCT/EP2010/066495, 4 pages.
(Continued)

*Primary Examiner* — Amara Abdi
(74) *Attorney, Agent, or Firm* — Morrison & Foerster LLP

(57) ABSTRACT

A method of filtering glints by processing an image of a user's cornea to obtain coordinates of desired glints from a configuration of light sources, comprising processing an image, in a first image space, of a user's cornea to determine coordinates of respective multiple positions of glints; and iteratively: selecting from the coordinates a first and a second set of coordinates; computing from the first set of coordinates a transformation that transforms the first set of coordinates into first coordinates of a predetermined spatial configuration; and testing whether the transformation transforms also the second set into positions that match second positions of the predetermined configuration. The coordinates of the desired glints are selected as those first and second sets which are transformed into coordinates that match the first and second coordinates of the predetermined configuration. The method is based on a geometrical homography and is expedient for robust gaze estimation in connection with e.g. eye tracking.

17 Claims, 4 Drawing Sheets

(51) Int. Cl.
*G06T 7/00* (2006.01)
*G06T 7/20* (2006.01)
*G06K 9/00* (2006.01)

(56) References Cited

U.S. PATENT DOCUMENTS

| | | | | |
|---|---|---|---|---|
| 2003/0123027 | A1* | 7/2003 | Amir | G06K 9/00604 351/209 |
| 2004/0189935 | A1* | 9/2004 | Warden | G02C 7/027 351/204 |
| 2004/0196214 | A1* | 10/2004 | Maguire, Jr. | G06F 3/013 345/8 |
| 2011/0182472 | A1* | 7/2011 | Hansen | A61B 3/113 382/103 |
| 2011/0228975 | A1* | 9/2011 | Hennessey | A61B 3/113 382/103 |

OTHER PUBLICATIONS

International Preliminary Report on Patentability received for PCT Patent Application No. PCT/EP2010/066495, issued on Feb. 28, 2013, 12 pages.

International Written Opinion received for PCT Patent Application No. PCT/EP2010/066495, mailed on Aug. 26, 2011, 4 pages.

Office Action received for European Patent Application No. 10784460.7, mailed on Sep. 24, 2014, 5 pages.

* cited by examiner

METHOD OF DETERMINING REFLECTIONS OF LIGHT

CROSS REFERENCE TO RELATED APPLICATIONS

This is a U.S. National Phase patent application of PCT/EP2010/066495, filed Oct. 29, 2010, which is hereby incorporated by reference in the present disclosure in its entirety.

BACKGROUND

As one of the most expressive features of the human face, eyes play an important role in interpreting and understanding a person's desires, needs, cognitive processes, and emotional states. The importance of eye gaze or simply gaze is implicitly acknowledged as it is used for inspection of our surroundings and is important in social interaction.

Reflections of light can be detected when observing a person's eye. Especially when the reflections are relatively distinct and confined in their expanse, they are also denoted glints; however, the term glints may also be used for any type of reflection or portion thereof.

Gaze estimation and tracking, also denoted eye tracking, are important for many applications including human attention analysis, human cognitive state analysis, gaze-based interactive user interfaces and gaze contingent graphical display. That is, for analysis and/or for interaction with machines such as dedicated apparatuses, general purpose computers with software, etc. Gaze estimation and tracking are used not only as means for persons with a disability preventing them from using conventional user interface means such as keyboards or pointing devices, but also for using gaze and eye movements in user interaction with machines.

Robust nonintrusive eye detection and tracking are therefore crucial to human computer interaction, attentive user interfaces and the understanding of human affective states. As the eye scans the environment or fixates on particular objects in the scene, an eye gaze tracker simultaneously localizes the eye position and tracks its movement over time to determine the direction of gaze. The term 'scene' is used for the physical field within which the gaze can be estimated or tracked by a device. The physical space can be any space in three dimensions or two dimensions, where the latter is typical for gaze directed to a display screen.

One class of methods for tracking eye gaze is based on corneal reflections of light. Corneal reflection gaze tracking systems project some pattern of light onto the cornea and then detect the position of the pupil or iris or other distinctive feature representing the eye's orientation relative to reflections of that light pattern. The reflections (also known as glints) of that light pattern are used as a spatial reference. Thus, a gaze tracking system determines e.g. the center of the pupil and the glints and the change in the distance and direction between the two as the eye is rotated. The orientation of the eyeball can be inferred from the differential motion of the pupil center relative to the glints. Visible light can be used, but near-infrared light is often employed, as users cannot see infrared light and are therefore not distracted by it.

The main components of a typical corneal reflection gaze tracking system comprise a video camera sensitive to near-infrared light, a near-infrared light source (often light-emitting diodes arranged in square configuration) mounted to emit light towards a person's eyes, and a computer system or other hardware system for analyzing images captured by the camera. Analyzing the images comprises detecting the position of the pupil or iris or other distinctive feature representing the eye's orientation and detecting reflections from the light pattern to determine the position of the pupil or iris or other distinctive feature relative to reflections of the light pattern which is used as a spatial reference. Image processing techniques comprising e.g. intensity threshold and edge detection are employed to identify the glints and the pupil from the image captured by the camera.

With so-called homography normalisation or similar methods it is possible to make an eye tracking apparatus that estimates where a person is looking in a way that is substantially invariant to the person's head movements. This means that it is possible to obtain a highly flexible eye tracker that is simple in its configuration and can be made compact and mobile.

Generally, gaze trackers based on corneal reflection are quite accurate and robust when used indoors. Most eye detection and gaze estimation methods used for gaze interaction rely on reflections (glints) of IR light sources on the cornea. Even though light conditions can to some degree be controlled by IR illuminators, the system still faces problems when used in less constrained settings (such as outdoors or in cars or when light comes from windows) since several indistinguishable reflections may appear on the cornea. In this situation it is not obvious which reflections belong to a predetermined configuration of light. The predetermined configuration of light is also denoted 'system light', whereas light from any other sources is denoted 'spurious light'.

PRIOR ART

The article "Homography Normalization for Robust Gaze Estimation in Uncalibrated Setups" presented at "The sixth Biennial Symposium on Eye Tracking Research & Applications" (ETRA 2010), http://etra.cs.uta.fi, by Dan Witzner Hansen et. al. discloses a gaze tracking system as mentioned above.

However, in many situations the user will be in an environment where many additional and different sources of light (inferior light sources) will impinge on the person's eyes and cause many reflections to be captured by the camera. Such additional sources giving spurious light, i.e. light sources in addition to the system light sources in a predefined configuration, can confuse an eye tracking system and disrupt reliable eye tracking. This is a problem. In an indoor environment such sources of light can be conventional indoor lamps, influx of daylight from windows and computer display screens, just to mention a few. In an outdoor environment, the sources of light can be sunbeams or reflections thereof, car's headlights, streetlight, etc.

SUMMARY

The method disclosed below filters an image of the cornea and reflections thereon to find a correct match of glints and light sources in a predefined configuration substantially regardless of head and eye orientation as long as the glints are present in the image.

It should be noted that an image can originate from a conventional camera of any type or, mutatis mutandis, from other types of 2D light sensors such as those detecting changes in light intensity and providing 'images' in the form of 2D event sequences or simply events.

There is disclosed a method of determining reflections of light to obtain coordinates of desired reflections from one or more predefined configuration(s) of light, comprising: processing an image of a living being's cornea to determine multiple coordinates of reflections of light, respectively; iteratively selecting, from the coordinates, a first and a second set of coordinates; computing from the first set of coordinates a transformation that transforms the first set of coordinates into first coordinates of a predetermined spatial configuration; and testing whether the transformation transforms also the second set into positions that match second positions of the predetermined configuration(s); and selecting the coordinates of the desired reflections to be those first and second sets which are transformed into coordinates that match the first and second coordinates of the predetermined configuration.

Consequently, the coordinates of the glints from the predefined configuration of system light are reliably distinguished from coordinates of spurious reflections from other, inferior light sources. The reliable determination of the desired glints makes it possible to use the glints as spatial references in an automated/computerized method. Thus, with this method, position and/or orientation of the reflective object relative to the position and orientation of the camera that takes the image and the position and orientation of the predefined configuration of light sources can be computed with improved reliability. Thereby, an eye tracking or eye detection system embodying the method will be more robust, i.e. far less sensitive to disturbances from other, inferior light sources. An eye tracking system can hence keep track of the gaze even when the image is distorted with reflections from inferior light sources.

A transformation is also produced that maps from the image, defined for the sake of reference to be in a first image space, to a second image space where the predefined configuration is defined to be located. In embodiments of the method, the first image space is simply an instance of an image, and the second image space is simply a collection of coordinates. In practical situations, any of the image spaces is identifiable as images, collections of coordinates or whatever representation is convenient for handling the information.

The configuration of light can be emitted by light sources of the type emitting visible light or invisible light, e.g. infrared light, and in both events they can be light emitting diodes (LEDs). The light sources are arranged in a predefined pattern, e.g. at the corners of an imaginary triangle, a square, a pentagon, hexagon, in a two-by-three dot pattern or another pattern. Ideally, the light source emitting system light will thus cause a glint configuration distinguishable from other, spurious, glints. In that case processing of the image is performed to determine coordinates of respective positional characteristics of multiple glints as e.g. a centre position of the light sources in image coordinates.

The configuration of light can alternatively be emitted by a display screen emitting e.g. a square-shaped field of light. In that case, processing of the image is performed to determine coordinates of respective positional characteristics of multiple glints as e.g. a position of the corners of the square shaped field in image coordinates. Other shapes of fields or faces of light can be used mutatis mutandis.

It provides a more robust system when the light sources or predefined pattern thereof are arranged substantially in one and the same plane.

The image can be recorded with a camera, e.g. a video camera of the CCD type such as a so-called web-camera which is frequently preinstalled in a laptop computer. The speed of the camera must be sufficiently high to capture movements of the reflective object such as the eyeball of a human being. Other types of cameras, Dynamic Vision Sensors (DVS) or 2D sensors or 3D sensors (see e.g. http://siliconretina.ini.uzh.ch) can also be used, mutatis mutandis. In case a conventional camera is used, a sequence of images is output, i.e. a sequence of frames of pixel intensity values. In case a Dynamic Vision Sensor is used, a sequence of (2D) events representing changes in intensity is output.

Coordinates of glints in the image, if any, are determined by image processing. Typically, glints appear as expressive features since they have a strong intensity in the image compared to other features of the image. Therefore the coordinates of a glint can be determined by threshold filtering the image to determine the expanse of the glint and then determining the coordinate of its position in the image, e.g. as the estimated centre of its expanse, as a lowermost point on its periphery or another predefined geometrical position of the glint. Alternatively, other image filtering techniques and geometrical computations known in the art can be applied to identify coordinates of the glints or coordinates of distinctive spatial features, such as apex of a triangle; acute and/or obtuse, inward or outward angled corners, etc., comprising temporal changes and image feature extraction. The result of determining coordinates can e.g. be in the form of a list of coordinates, a binary image or an image representing the likelihood that a glint is present in the image. The configuration of light, i.e. system light, may be provided by multiple distinctive light marks or fewer, e.g. one mark with several, at least three, geometrical features, e.g. the three corners of a triangle shape or the vertices of a star-shape etc. The configuration of light can have colours. To determine coordinates of spatial features of a configuration of light, colour information can be taken into account in image processing. In the case of multiple distinctive light marks, coordinates are determined to be the position of e.g. the centre of the marks, whereas, in the latter case, coordinates are determined to represent e.g. the corners of a triangle or the vertices of a star.

As a first step of an iterative procedure, a first and a second set of coordinates are selected from the determined coordinates. The first set is used to compute a transformation, and the second set is used to test the transformation.

The transformation is computed from the first set of coordinates and coordinates of the predetermined spatial configuration. The transformation transforms one set of coordinates to another set of coordinates, linearly or non-linearly. A transformation can be a projective transformation such as a collineation, homographic transformation, a Möbius transformation, an affine transformation or be of another type. For computing the transformation, the coordinates may be represented as homogeneous coordinates. For a linear transformation, coefficients of the transformation can be computed deterministically.

The predetermined configuration can be represented by a set of coordinates, e.g. homogeneous coordinates, or by an image, e.g. a binary image, monotone image or colour image. In case the predefined configuration has four distinct light marks, the first set of coordinates may count three (3) coordinates and the second set one (1) coordinate at which a glint is found to be located in the image. Thus, the predefined configuration counts four (4) coordinates, i.e. the sum of counts of the first and second set. The predefined configuration in terms of its coordinate representation expediently has approximately the same layout as the physical layout of the configuration of light.

Testing whether the computed transformation transforms also the second set into positions that match second positions of the predetermined configuration is a test to decide if the coordinates in the first and second set are of glints that originate from the predefined configuration of light. This is decided by testing whether there exist a transformation and a first and a second set of coordinates that map to the predefined configuration. The first and/or second set are/is selected differently until a match, if any, is found.

Whether the transformation transforms also the second set into second positions of the predetermined configuration is tested e.g. by transforming coordinates of the second set with the computed transformation and verifying the transformed coordinates against the second positions of the predetermined configuration or a space around the second positions. Verification is performed e.g. by computing a measure of the probability that the transformed coordinates are coincident with the second positions of the predetermined configuration, e.g. comprising computing a measure of the distance between respective transformed coordinates and second positions of the predetermined configuration. Discrimination between a match and 'no match' is e.g. performed by a threshold discriminator.

This procedure is repeated for different combinations of coordinates in the first and second set until a match, if any, is found. The different combinations can be generated in various ways. From all coordinates of glint positions, the first and the second set of coordinates are extracted, and a set of residual coordinates comprises the remaining coordinates. Then coordinates can be shifted between the first and second sets and between the first or second set and the residual coordinates to try different combinations. As an example, so-called priority search trees can be used to structure generation of different combinations. It should be noted that all permutations of a combination of coordinates in the estimation set do not have to be tested in every situation. For the generation of combinations, it is possible to use a geometrical or spatial search to locate coordinates of glints that satisfy some geometrical or spatial constraints implied by the physical configuration of the system light. Such a constraint may be that a certain minimum and/or maximum distance between two coordinates is expected and/or that a specified direction or range of directions between coordinates is expected.

When a match is found, the coordinates of the desired glints are determined. Those coordinates can reliably serve as reference coordinates. In combination with feature extraction from the image, positional or directional information can be computed.

For instance in connection with computing positional or directional information, the transformation that transformed the coordinates to a match can be of use for computations in an image space where the predetermined configuration is defined.

Thus, in an embodiment, the method comprises applying the transformation that is tested to transform also the second set to transform the image, selected portions thereof or image features into a second image space. This second image space is also denoted a normalised image space (see "Nomography Normalization for Robust Gaze Estimation in Un-calibrated Setups" by Dan Witzner Hansen et. al.). Different ways of extracting distinctive image features of the human being are known in the art. When these features are transformed to the second image space, also denoted a normalised image space, orientation of the human eye can be determined with reference to the coordinates of the predefined configuration in a way that is substantially invariant to the human being's head pose when an appropriate transformation is used. At least when the image is recorded in the infrared light range, the pupil of the eye is an example of such a distinctive feature to extract.

In an embodiment, the method comprises applying a further transformation that transforms image data of the second image space to a third image space, where the transformation is computed from respective inter-related coordinates of calibration targets in the third image space and pupil positions computed from image data in the second image space. The transformation may be a linear or non-linear transformation.

In case of eye gaze estimation, the third image space is easily defined in coordinates that relate to a physical scene beheld by the user, e.g. a computer display screen or another object which is subject to the eye's gaze. This third image space is also denoted a physical image space (see "Homography Normalization for Robust Gaze Estimation in Un-calibrated Setups" by Dan Witzner Hansen et. al.).

The third image space and the transformation between the second and third image space are convenient since they allow transformation of computed positions of regard in the second image space to be transformed to meaningful physical coordinates (see the published application WO10/003,410 A1). The transformation is estimated from observations of points of regard in the second (normalised) image space and respective calibration targets. Calibration targets may be visual objects being successively subject to the user's gaze, while the gaze is determined from image recordings. On a computer display this is conveniently performed by making objects successively visible.

The predetermined configuration is alternatively defined directly in the third or physical image space in which case the second or normalised image space is not needed or the second image space is coincident with the third image space.

In an embodiment, matching comprises computing an indicator representing whether the second set of coordinates falls within a predetermined field of the second image space located about at least one of the second positions of the predetermined configuration. The predetermined field can be a square, a circle, an ellipse or be of another shape which represents a spatial confidence range setting the bounds for determining whether there is a match or not.

A further measure can optionally comprise computing a measure representing the distance from the transformed position to the target position. Still further measures for determining a match can optionally comprise comparing a shape of a glint to an expected shape and/or comparing image intensity at or about the position of the glint to an expected image intensity and/or comparing colour or texture at or about the position of the glint, or any combination thereof.

Still further measures for determining a match can comprise evaluating parameters or combinations thereof of the transformation. The parameters of the transformation can represent scaling, displacement, rotation and warping/skewness. The parameters can be evaluated against a threshold value or a threshold range.

In an embodiment the method comprises processing the image to compute an image feature such as a position or circumference of the user's pupil or iris/limbus in the image; and transforming the image feature into a second image space with the transformation that is tested to transform also the second set.

Alternatively, image data can be directly transformed to the second image space.

In an embodiment processing of the image comprises identifying in the image a field where at least one of the user's eye pupils is present; where the field is defined to have a smaller size than the image; and where processing to compute an image feature such as a position or circumference of the user's pupil in the image is confined to the field.

In this way the computational effort in computing a distinctive eye feature can be reduced.

In an embodiment the method comprises using the coordinates of respective multiple positions of glints as a starting point in the image for an algorithm that computes an image feature that represents the user's pupil, such as a position or circumference of the user's pupil.

Since light reflections are salient features compared to other features of the human eye, surrounding skin or other parts of the human face, a simple processing of the intensity values (e.g. comprising thresholding) of the image can reveal glint locations on the eye and thus in a computationally efficient way detect the location of an eye.

The filtering method in itself can also be used as a method to detect an eye. Then, when a match is found, the eye is determined to be at or about the position of the glints that transformed successfully. Subsequently, the position of those glints can be used as a starting point in the image for an algorithm that computes an image feature that represents the user's pupil, such as a position or circumference of the user's pupil.

Avoid Trying all Combinations

In an embodiment of the method, in a first image, a first set of coordinates and a second set of coordinates, which are tested to transform into positions that match positions of the predetermined configuration, are stored; then, for a subsequently recorded image, the first and second set of coordinates are used as starting points for finding a subsequent set of first and second coordinates of glints located within the closest distance to the starting points.

Thereby locations of glints in a first image can be used as an educated guess of where the glints are located in a second image recorded later. This can reduce the computational effort. This, however, presumes that the images are recorded at close points in time since the human eye moves relatively quickly. The educated guess on where the glints are located can be performed in the space of the recorded image or the first or second image space.

In an embodiment of the method, it relates to performing gaze estimation comprising, along with the transformation that is tested, to also transform the second set into positions that match second positions of the predetermined configuration, computing a position or direction of regard.

The direction of regard or gaze direction is computed e.g. as the so-called optical axis or the so-called visual axis. The optical axis is the line connecting the pupil centre, cornea centre and the eyeball centre. The line connecting the fovea and the centre of the cornea is the visual axis.

The light sources, i.e. the system light, provide a spatial reference for the gaze estimation or estimation of the orientation of any other light reflective object. Therefore, if the system light is moved relative to the physical scene, a computed direction or position of regard changes accordingly. Other means for taking a movement of the system light and thus the spatial reference into account can be provided.

In an embodiment of the method, multiple sets of coordinates of respective predetermined spatial configurations are defined, where the spatial configurations have patterns that are mutually different from each other; and steps of the method are repeated to determine a set of desired coordinates along with an identification of that respective spatial configuration for which the desired coordinates match the first and second coordinates.

Consequently, it is possible to identify which of respective patterns is/are recognizable by their reflections. This reliable identification makes it possible, in an alternative way, to compute an individual's gaze. When the predefined configurations of light are placed at different locations, it is possible to infer where the individual is looking.

If the configurations of light, one or more at a time, occur as reflections of light on the cornea, determination of a particular one or particular ones of respective ones of the multiple configurations, with knowledge of its spatial location in the real world, can be used to compute the individual's gaze, i.e. simply by determining which configuration or configurations is/are recognizable. Thus, in some embodiments this is performed simply by identifying which of the configurations that are detected. This may give a simple indication of where the person is looking since the location of the configurations is predetermined.

This method of gaze estimation can be combined with computing gaze from the determination of a distinctive feature of the eye, e.g. iris or pupil, and using one or more of the predetermined configurations as spatial references. A gaze direction can be identified as the pattern where the pupil centre is closest to the centre of pattern; the gaze direction then being given by identification of that pattern. A gaze direction can also be computed from the pupil's orientation relative to several patterns.

This is applicable e.g. in a car to determine t the focus of a driver's attention. As an exemplary embodiment, a system according to the method can comprise a first system light unit emitting a first pattern of light located in the left side view mirror, a second unit with a second pattern in the right side view mirror, a third unit with a third pattern in the rear view mirror, and a fourth unit with a fourth pattern in front of the driver.

Additionally, there is disclosed:

A data processing system having stored thereon program code means adapted to cause the data processing system to perform the steps of the above method, when said program codes means are executed on the data processing system;

A computer program product comprising program code means adapted to cause a data processing system to perform the steps of the above method, when said program code means are executed on the data processing system;

A computer program product, comprising a computer-readable medium having stored thereon the program code means;

A computer data signal embodied in a carrier wave and representing sequences of instructions which, when executed by a processor, cause the processor to perform the steps of the above method; and A semiconductor product comprising a circuit configuration adapted to cause the semiconductor product to perform the steps of the above method, when electrically powered and connected to a computer system with a camera.

BRIEF DESCRIPTION OF THE DRAWING

A detailed description will be given in the below with reference to the drawing, in which.

DETAILED DESCRIPTION

Figure 1:
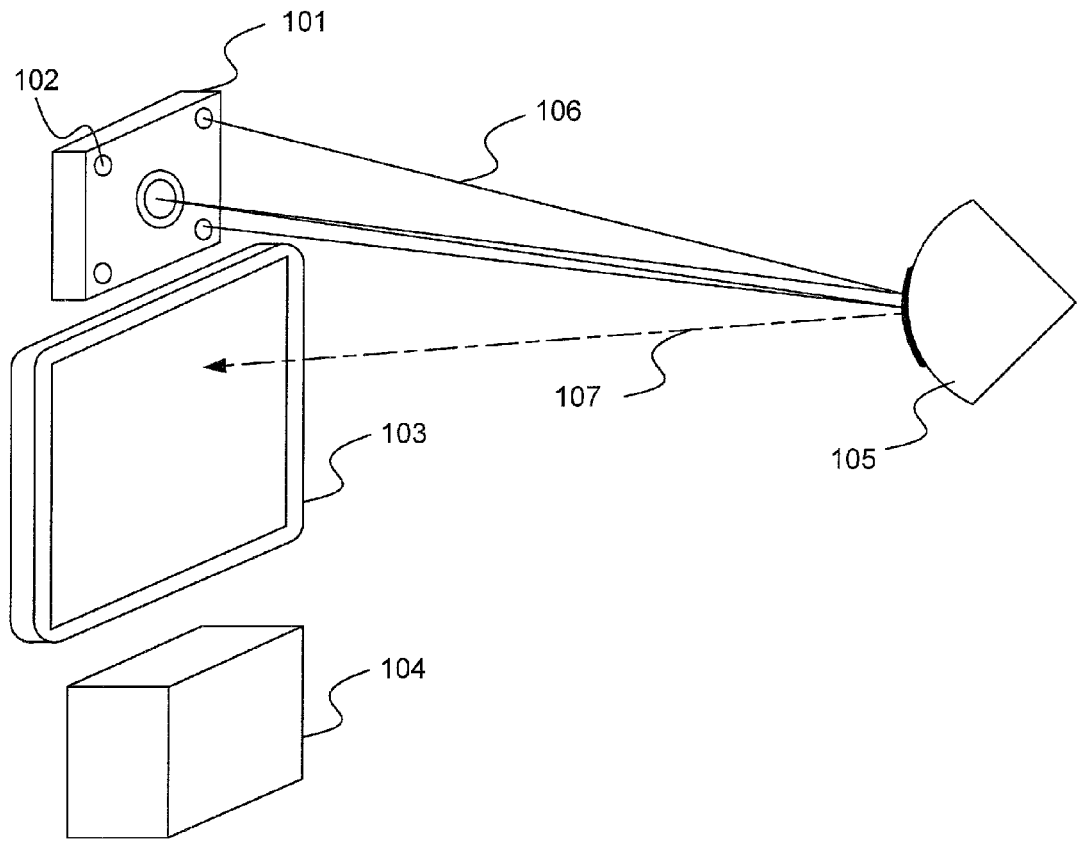
FIG. 1 shows a physical setup of a system for gaze estimation.

FIG. 1 shows a setup of a system for gaze estimation. The system comprises a camera 101, a configuration of light sources 102, a display screen 103 and a computer 104. A portion 105 of a human being's eye ball is illustrated, where light beams 106 illustrate that light is emitted by the light sources 102 and reflected on the eye ball back to the camera 101. For simplicity, light beams from only two of the four light sources 102 are shown. The dashed line 107 illustrates the eye's gaze direction which may be the visual or optical axis. An image is recorded by the camera and the light incident on the eye ball appears as glints in the image. It should be noted that camera and light sources (system light) do not necessarily have to be in the same plane.

The computer 104 is coupled to the display screen 104 and the camera 101 to acquire images by means of the camera and is loaded with a programme to perform eye detection and gaze tracking. The computer may be loaded with other programmes for simultaneously performing other functions. Eye gaze tracking localizes an eye's position in an acquired image and tracks its movement over time to determine the direction of gaze.

The computer is also programmed to calibrate eye gaze tracking such that the error in estimating eye gaze tracking is reduced. A method of calibration is disclosed e.g. in the published application WO10/003,410 A1. Calibration is achieved e.g. by displaying objects at different locations on the display screen and asking the user to direct his/hers gaze to that object or a point at that object. The physical scene for eye gaze tracking is typically confined e.g. to the area of the display screen. However, the physical scene can be a scene of other objects than a display screen and may comprise multiple objects, e.g. technical installations, a printed media, etc.

As shown, the predefined configuration of light is embodied as four distinct light sources mounted in a camera body. Alternative layouts or patterns of the distinct light sources are possible, e.g. a two-by-three pattern, a dot-line pattern etc. The light sources or the light pattern need not be in the one and same plane, the pattern or light sources can be arranged e.g. on or as a portion of a sphere.

The predefined configuration of light can alternatively be configured as a luminous face with a certain shape, e.g. a polygon with distinct corners and edges, e.g. a square, a rectangle, a pentagon etc. A display screen for a computer may constitute such a luminous face.

The camera is a digital camera, e.g. of the CCD type, and provides a succession of images with multiple images per second. The camera and light sources are mutually configured to detect and emit visible light and/or infrared light.

Figure 2:
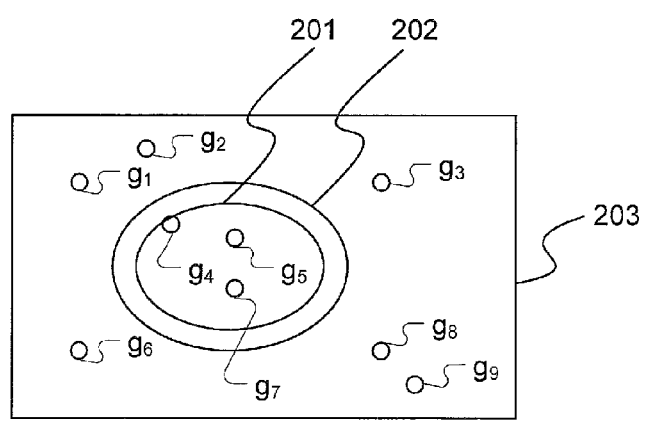
FIG. 2 illustrates an image acquired in the physical setup.

FIG. 2 illustrates an extract of an image acquired in the physical setup. The image acquired from the camera typically captures at least the human being's head and more. Thereby head movements are possible within the field of view of the camera, while the camera remains in a fixed position with respect to the light sources. Therefore extracts from the image which are relevant to eye gaze estimation are provided by image processing methods known in the art.

The image extract 203 shows a section of the eyeball where glints from various light sources are shown. The glints are shown as circles, but are of course of any shape depending on the light sources. The glints are designated $g_1, g_2, \ldots g_9$. Eye features, such as the eye pupil, are designated reference numeral 201 and the fovea reference numeral 202.

Thus, the image extract 203 illustrates a result after image processing of an image acquired from the camera 101 to identify an eye or eye section.

Figure 3:
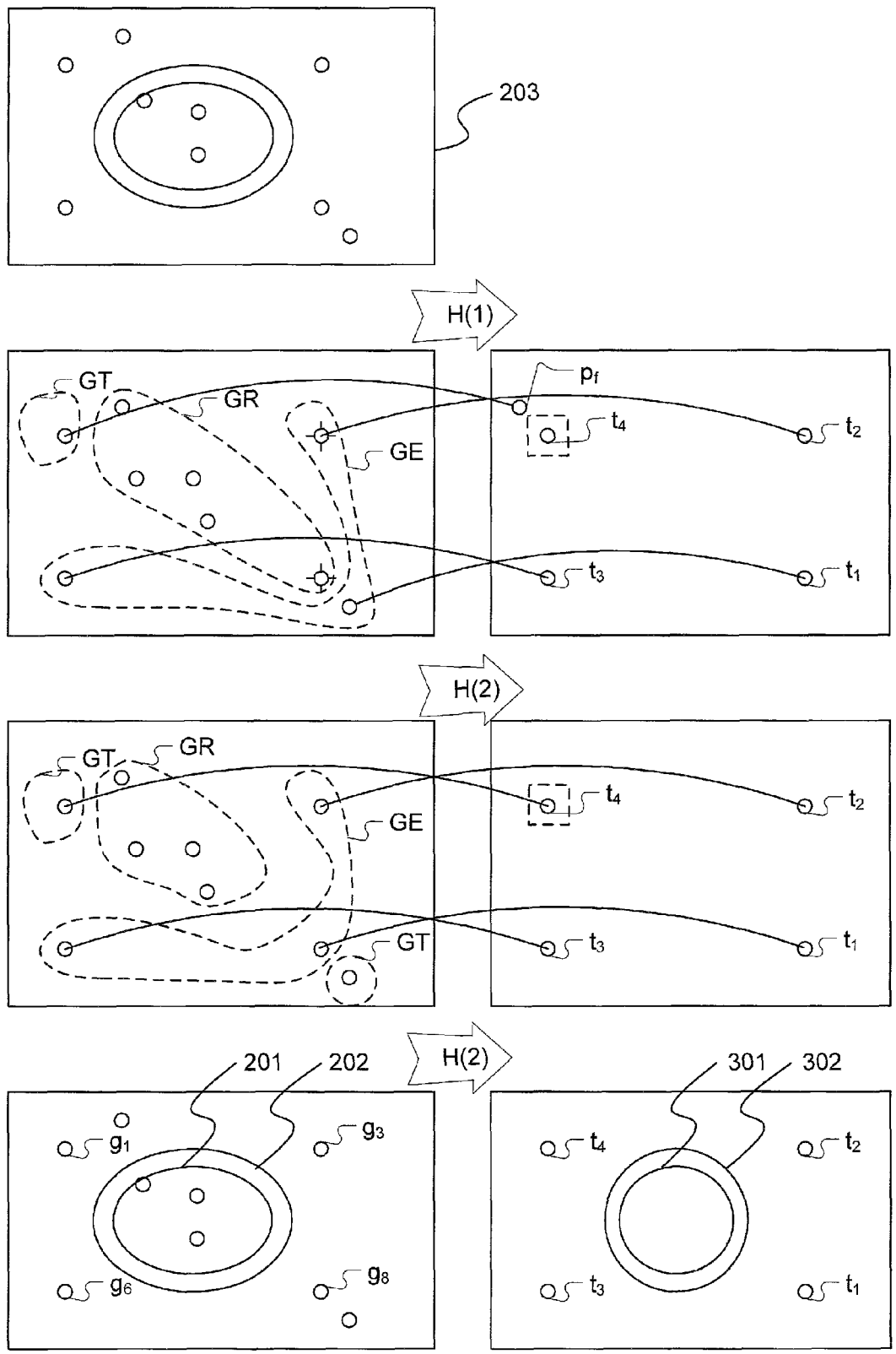
FIG. 3 illustrates glint filtering.

FIG. 3 illustrates glint filtering. An image extract 203 is shown topmost on the left. It comprises eye features and glints as shown in FIG. 2. The glints are shown in the image extract, but for computing purposes their representation comprises coordinates, e.g. homogeneous coordinates.

Below the image extract 203, on the left hand side, is shown an exemplary result of selecting a first and second set of coordinates. The first set is denoted GE and the second set is denoted GT. The glints remaining after selecting the first and second set are denoted GR.

On the right hand side is shown an image space with four target points: $t_1, t_2, t_3$, and $t_4$. The first three target points are used in combination with the first set of coordinates GE to compute a first transformation H(1) in a first step of an iterative process. It is shown by curved lines that the coordinates of GE are transformed to $t_1, t_2$ and $t_3$. The transformation can be an affine transformation (homography) or another type of linear or non-linear transformation.

It is then, with this transformation H(1), tested whether the coordinate(s) of GT transforms to $t_4$. As illustrated, the coordinate in GT transforms to a point $p_f$. Testing is performed by verifying the transformed coordinate $p_f$ against the second position $t_4$ of the predetermined configuration or a space around the second position as illustrated with a dashed-line box. The test reveals that there is no match, since $p_f$ falls outside the dashed-line box. The box is alternatively a circle or ellipse or of another shape.

The set GT is then replaced by selecting a coordinate from GR, and GT is transformed by H(1) to determine if there is a match with $t_4$. This process is continued until a match is found or all coordinates of GT have been tested. In the latter event, the set GE is replaced partly or fully.

Further below, it is shown that the set GE is replaced by substituting one of the coordinates in GE with one of the coordinates in GR—shown in the lower rightmost corner of the image fraction. Thus, GE then comprises a new combination or instance of coordinates. From this new instance, a new transformation H(2) is computed.

With this transformation H(2), it is then tested whether the coordinate(s) of GT transforms to $t_4$. As shown, this test is positive since the coordinate of GT is transformed right on to $t_4$. The test would also have been positive if the coordinate transformed into the area of the surrounding dashed-line box. This test can also be a classification, e.g. a binary classification.

Since the test of H(2) was positive with the coordinates selected in the instance of GE and GT, the coordinates of the glints from the predefined configuration of light sources are known. These coordinates are desired in order to obtain a reference for computing the position of eye features. As can be seen, $g_1, g_3, g_6$ and $g_8$ are determined as the coordinates of the glints from the predefined configuration of light sources.

As shown lowermost, H(2) is applied to transform features 201 and 202 of the image extract to a the second image space where the four target points: $t_1, t_2, t_3$, and $t_4$ serve as spatial references. The transformed features are designated 301 and 303.

The offset at which the image extract is located in the acquired image may also be information for the spatial reference.

Figure 4:
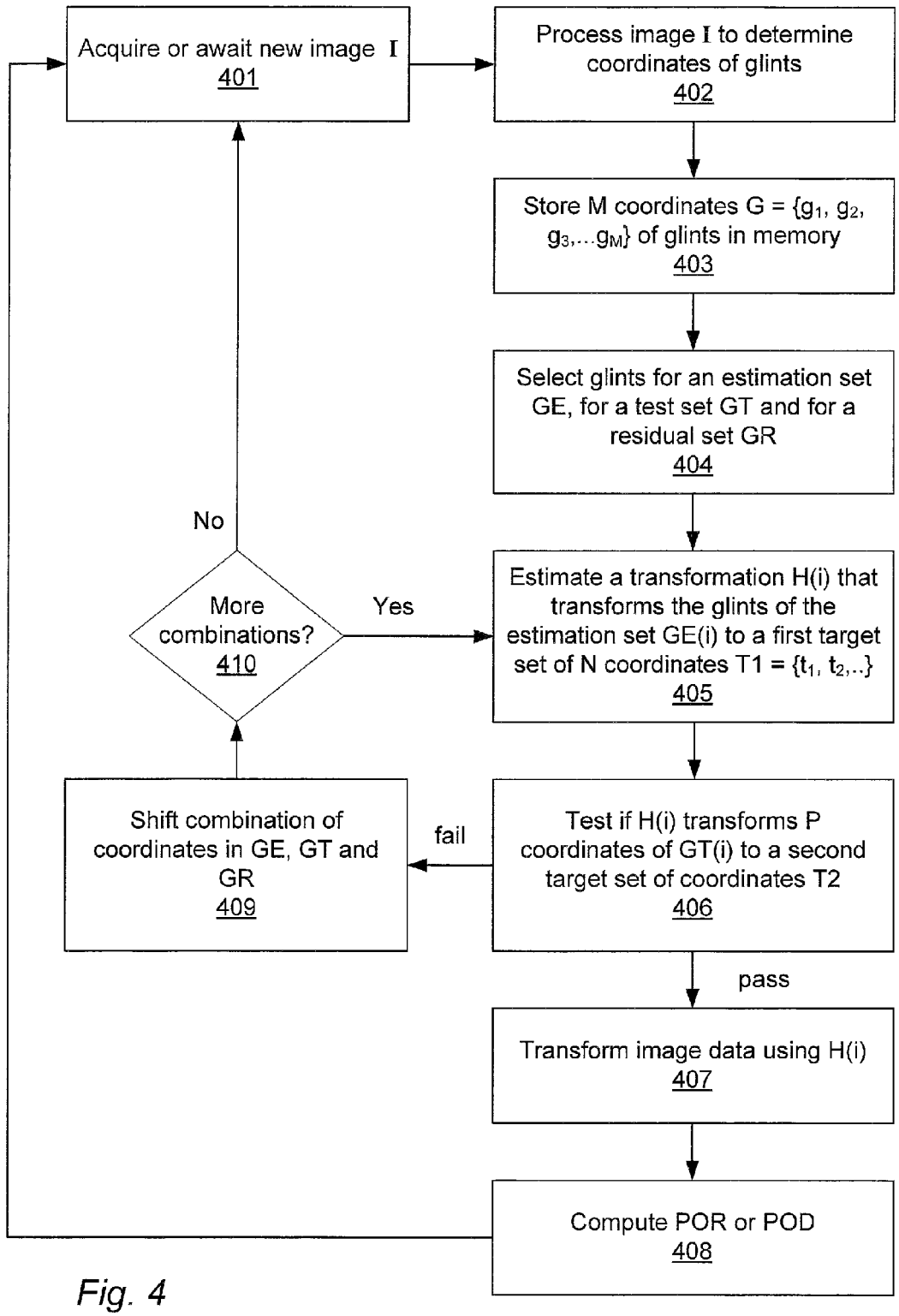
FIG. 4 shows a flowchart for glint filtering.

FIG. 4 shows a flowchart for glint filtering. The flowchart illustrates an exemplary embodiment of the method of filtering glints.

In step 401 an image I is acquired in the sense that either it is requested by a component of the eye tracking system or it is pushed from the camera. In step 402 the image I is processed to determine coordinates of glints. This processing may comprise a step where a portion of the image is extracted such as a portion with an eye. The location of the extracted image in the acquired image I is recorded for the purpose of determining a spatial reference relative to the camera.

A set of M of coordinates $G=\{g_1, g_2, \ldots g_{M\_k}\}$ is stored in a memory as a result of determining glints in step 401. This set comprises coordinates of all glints, i.e. {GE, GT, GR}.

From the set of all glints, coordinates for an estimation set GE and a test set GT are selected in step 404. The remaining coordinates are comprised by a residual set GR.

In step 405 a transformation H(i) that transforms the coordinates of the estimation set to coordinates of target points of the predefined configuration of light is computed. The index I indicates the current iteration of an iterative process. The transformation is computed (also called estimated) by means of methods known in the prior art. The transformation may be a similarity transformation or an affine transformation or a Möbius/homographic transformation or another transformation. A transformation may be e.g. an affine transformation comprising one or more of rotation, scaling, shear and translation or combinations thereof.

In subsequent step 406 it is tested whether the transformation H(i) transforms also coordinates of the test set GT into the coordinates of the target points. As mentioned, this test can be performed in various ways, e.g. by including a region about the target points and within which transformed points are accepted as matching; alternatively by computing a measure of the likelihood that the transformed point is matching a target point.

If there is a match, i.e. a pass, the method proceeds to step 407 where coordinates of desired glints i.e. the glints from the predetermined configuration, are stored in memory. Subsequently, the image I, an extracted image thereof or extracted features are transformed to the second image space using H(i). In step 408 a position of regard or direction of regard is computed. The result thereof may be stored in a memory accessible for another hardware system or a software application or conveyed thereto in another way known in the art. Additionally or alternatively, the transformation H(i) or properties (such as one or more from the group of: scale, rotation, displacement, and shear) thereof can stored in a memory accessible for another hardware system or a software application or conveyed thereto in another way known in the art.

If there is not a match, i.e. a fail, the method proceeds to step 409 where the combination of coordinates in GE and/or GT and/or GR is shifted. Subsequently, it is tested in step 410 if there are more combinations to try in the iterative procedure. If there are more combinations to try, the method reverts to step 405 with a new combination. If not, the method proceeds to step 401 to await or request a new image.

Between step 407 and step 408 there may be an additional step of transforming coordinates from the second image space to a third image space. In this case, POR or DOR computation is performed on coordinates in the third image space.

As mentioned above, in an embodiment of the method, multiple sets of coordinates of respective predetermined spatial configurations are defined, where the spatial configurations have patterns that are mutually different from each other; and steps of the method are repeated to determine a set of desired coordinates along with an identification of that respective spatial configuration for which the desired coordinates match the first and second coordinates. Consequently, it is possible to identify which of respective patterns that is/are recognizable by their reflections. In an embodiment thereof, the target sets T1 and T2 of coordinates in step 405 are extended to target sets $T1_j$ and $T2_j$ where index j designates a respective one of the configurations represented by $T1_j$ and $T2_j$ in combination. When more configurations can be present at the same time as reflections in the individual's eye, there can be multiple transformations $H_j(i)$, where index j designates a respective one of the configurations. The method can thus comprise an additional loop with step 405 and step 406 to iterate over the configurations. When the loop has finished all configurations, there are different options for proceeding with the method. One option is to proceed to step 409 if none of the configurations was matched and otherwise to proceed to step 407 along with an indication (e.g. represented by the value of index j) of a respective configuration. A further option is to proceed to step 409 when all combinations of coordinates have been tried against all configurations. A still further option is to set a limit of two, three or more configurations to try and then continue to step 407.

When multiple configurations are defined and identification of which of the multiple configurations that is detected is performed, the step 407 of transforming image data using Hj(i) can be skipped since eye features are not needed. Otherwise the method is modified mutatis mutandis.

Figure 5:
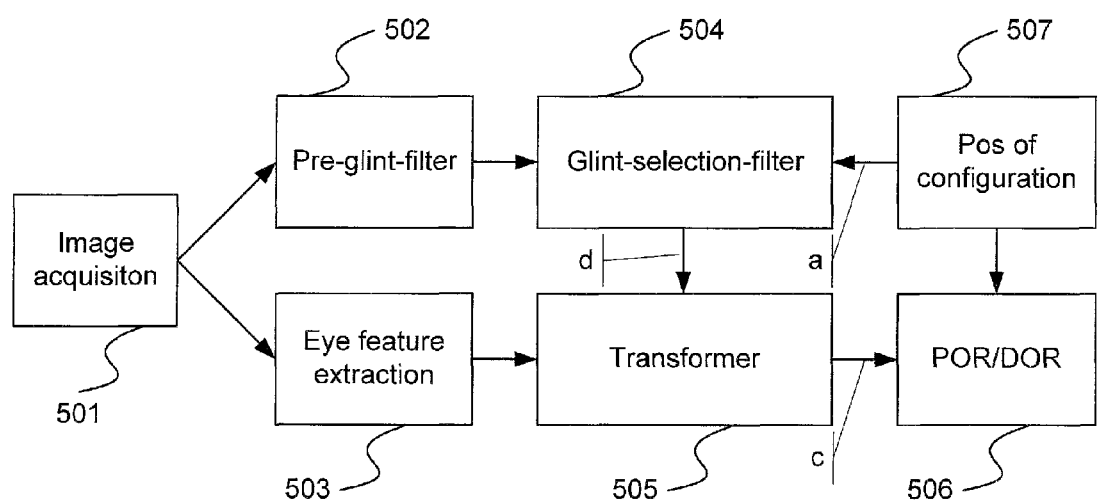
FIG. 5 shows components for filtering and gaze estimation.

FIG. 5 shows components for filtering and gaze estimation. The components comprise an image acquisition component 501 which provides an image for a pre-glint filter that determines coordinates of glints in the image. The glint selection filter 504, eye feature extraction, transformer 505 and POR/DOR component 506 operate as disclosed in connection with the flowchart. The component 507 provides positions of the predetermined configuration of light for performing the filter method and for computing POR/DOR.

The components are implemented e.g. in software loaded on a data processing system such as a general purpose computer.

In an embodiment the method is embodied as a data processing system having stored thereon program code means adapted to cause the data processing system to perform the steps of the above method, when said program codes means are executed on the data processing system. In some embodiments, the data processing system comprises e.g. a mobile telephone, a general purpose computer such as a laptop computer, and a computer dedicated to a special purpose. The system light may be a part of the data processing system.

A study of eye tracking systems can be found in e.g.:
 "Homography Normalisation for robust Gaze Estimation in Uncalibrated Setups" by Dan Witzner Hansen et. al.; and in
 "In the Eye of the Beholder: A Survey of Models for Eyes and Gaze" by Dan Witzner Hansen;
and their disclosed citations.

The book "Multiple View Geometry in Computer Vision" by R. Hartley and A. Zisserman, Cambridge University Press, 2003 provides further details for selecting and estimating appropriate transformations.

The invention claimed is:

1. A method of determining reflections of light to obtain coordinates of desired reflections from a predefined configuration of light, comprising:
 processing an image of an individual's cornea to determine multiple coordinates of reflections of light, respectively;
 iteratively:
  selecting from the coordinates a first and a second set of coordinates;
  computing from the first set of coordinates a transformation that transforms the first set of coordinates into first coordinates of a predetermined spatial configuration; and
  testing whether the transformation transforms also the second set into positions that match second positions of the predetermined configuration;
 selecting the coordinates of the desired reflections to be those first and second sets which are transformed into coordinates that match the first and second coordinates of the predetermined configuration.

2. A method according to claim 1, further comprising: applying the transformation that is tested to transform also the second set to transform the image, selected portions thereof or processed image data thereof into a second image space.

3. A method according to claim 2, further comprising: applying a further transformation that transforms image data of the second image space to a third image space, wherein the transformation is computed from respective inter-related coordinates of calibration targets in the third image space and pupil positions computed from image data in the second image space.

4. A method according to claim 1, wherein matching comprises computing an indicator representing whether the second set of coordinates falls within a predetermined field of the second image space located about at least one of the second positions of the predetermined configuration.

5. A method according to claim 1, further comprising:
processing the image to compute an image feature; and
transforming the image feature into a second image space with the transformation that is tested to transform also the second set.

6. A method according to claim 1,
wherein processing of the image comprises identifying in the image a field where at least one of the user's eye pupils is present,
wherein the field is defined to have a smaller size than the image, and
wherein processing to compute an image feature in the image is confined to the field.

7. A method according to claim 1, further comprising using the coordinates of respective multiple positions of glints as a starting point in the image for an algorithm that computes an image feature that represents the user's pupil.

8. A method according to claim 1, wherein, for a first image, a first set of coordinates and a second set of coordinates, which are tested to transform into positions that match positions of the predetermined configuration, are stored; then, for a subsequently recorded image, the first and second set of coordinates are used as starting points for finding a subsequent set of first and second coordinates of glints located within the closest distance to the starting points.

9. A method of performing gaze estimation according to claim 1, further comprising: with the transformation that is tested to transform also the second set into positions that match second positions of the predetermined configuration, computing a position or direction of regard.

10. A method according to claim 1,
wherein multiple sets of coordinates of respective predetermined spatial configurations are defined, wherein the spatial configurations have patterns that are mutually different from each other; and
wherein steps of the method are repeated to determine a set of desired coordinates along with an identification of that respective spatial configuration for which the desired coordinates match the first and second coordinates.

11. A data processing system having stored thereon program code means adapted to cause the data processing system to perform the steps of the method according to claim 1, when said program codes means are executed on the data processing system.

12. A non-transitory computer program product comprising program code means adapted to cause a data processing system to perform the steps of the method according to claim 1, when said program code means are executed on the data processing system.

13. A non-transitory computer program product according to claim 11, comprising a computer-readable medium having stored thereon the program code means.

14. A semiconductor product comprising a circuit configuration adapted to cause the semiconductor product to perform the steps of the method according to claim 1, when electrically powered and connected to a computer system with a camera.

15. The method of claim 5, wherein the image feature is a position or circumference of the user's pupil in the image.

16. The method of claim 6, wherein the image feature is a position or circumference of the user's pupil in the image.

17. The method of claim 7, wherein an image feature that represents the user's pupil is a position or circumference of the user's pupil.

* * * * *